US006312898B1

(12) United States Patent
Koulu et al.

(10) Patent No.: US 6,312,898 B1
(45) Date of Patent: *Nov. 6, 2001

(54) DIAGNOSIS OF A PERSON'S RISK OF DEVELOPING ATHEROSCLEROSIS OR DIABETIC RETINOPATHY BASED ON LEUCINE 7 TO PROLINE 7 POLYMORPHISM IN THE PREPRO-NEUROPEPTIDE Y GENE

(75) Inventors: Markku Koulu; Matti Karvonen; Ullamari Pesonen, all of Turku; Matti Uusitupa, Kuopio, all of (FI)

(73) Assignee: Hormos Medical Oy, Ltd. (FI)

( * ) Notice: Subject to any disclaimer, the term of this patent is extended or adjusted under 35 U.S.C. 154(b) by 0 days.

This patent is subject to a terminal disclaimer.

(21) Appl. No.: 09/291,994

(22) Filed: Apr. 15, 1999

(51) Int. Cl.$^7$ .............................. C12Q 1/68; C12Q 3/00; C02H 21/02
(52) U.S. Cl. ................................... 435/6; 435/4; 435/7.1; 536/23.1
(58) Field of Search .................. 435/6, 252.3, 320.1, 435/7.1, 455; 536/23.1, 24.3, 23.5, 24.5; 800/8, 9

(56) References Cited

U.S. PATENT DOCUMENTS 5,455,164 10/1995 Turner ................................ 435/240.2

FOREIGN PATENT DOCUMENTS 9527782 10/1995 (WO) .
9850563 11/1998 (WO) .

OTHER PUBLICATIONS

Chew, E.Y. et al. (1996) "Association of elevated serum lipid levels with retinal hard exudate in diabetic retinopathy." *Arch. Ophthalmol.* 114:1079–1084.

Ito, H. et al. (1996). "Risk factor analysis for macrofasclar complication in nonobese NIDDM patients: multiclinical study for diabetic macroangiopathy (MSDM)." *Diabetes* 45 Suppl. 3:S19–S23.

Ueda, H. et al. (1993). "Importance of serum cholesterol level in development of diabetic autonomic neuropathy." *Diabetes Res. Clin. Practice* 21:123–126.

Uusitupa, M.I.J. et al. (1998). "Neuropeptide Y: a novel link between the neuroendocrine system and cholesterol metabolism." *Ann. Med.* 30:508–510.

Karvonen, M.K. et al. (1998). "Association of a leucine(7)–to–proline(7) polymorphism in the signal peptide of neuropeptide Y with high serum cholesterol and LDL cholesterol levels." *Nature Medicine* 4:1434–1437.

Roche, C. et al. (1997). "Genetic studies of neuropeptide Y and neuropeptide Y receptors Y1 and Y5 regions in morbid obesity." *Diabetologia* 40:671–675.

Thorsell, A. et al. (1996). "Cationic lipid–mediated delivery and expression of prepro–neuropeptide Y cDNA after intraventricular administration in rat: feasibility and limitations." *Regulatory Peptides* 61:205–211.

Nystrom, F. et al. (1996). "A Population Study of Plasma Neuropeptide Y: Correlations with Components of the Metabolic Syndrome." *Blood Pressure* 5:349–353.

Minth, C.D. et al. (1984). "Cloning, characterization, and DNA sequence of a human cDNA encoding neuropeptide tyrosine." *Proc. Natl. Acad. Sci. USA* 81:4577–4581.

Larhammar, D. et al. (1987). "Structure and expression of the rat neuropeptide Y gene." *Proc. Natl. Acad. Sci. USA* 84:2068–2072.

Erickson, J.C. et al. (1996). "Attenuation of the obesity syndrome of ob/ob mice by the loss of neruopeptide Y." *Science* 274:1704–1707.

Jaenisch, R. (1988). "Transgenic Animals." *Science* 240:1468–1474.

*Primary Examiner*—Deborah J. R. Clark
*Assistant Examiner*—Eleanor Sorbello
(74) *Attorney, Agent, or Firm*—Rothwell, Figg, Ernst & Manbeck, p.c.

(57) ABSTRACT

The invention relates to methods for diagnosing a person's susceptibility for having an increased risk for the development of atherosclerosis and a diabetic person's susceptibility for having an increased risk for the development of diabetic retinopathy. The invention relates further to methods for treating persons diagnosed for having increased risk for the development of said diseases, in order to prevent the development of said diseases. The invention also concerns methods to investigate or screen pharmaceuticals or genetic aims useful in the treatment of said diseases, by using an animal model including a transgenic animal.

6 Claims, 3 Drawing Sheets

HUMAN NEUROPEPTIDE Y (NPY) GENE

EXON 1 (M14295)

```
1   ccgcttcttc aggcagtgcc tggggcggga gggttggggt gtgggtggct ccctaagtcg
61  acactcgtgc ggctgcggtt ccagccccct cccccgcca ctcaggggcg ggaagtggcg
121 ggtgggagtc acccaagcgt gactgcccga ggcccctcct gccgcggcga ggaagctcca
181 taaaagccct gtcgcgaccc gctctctgcA CCCCATCCGC TGGCTCTCAC CCCTCGGAGA
241 CGCTCGCCCG ACAGCATAGT ACTTGCCGCC CAGCCACGCC CGCGCGCCAG CCACCGTGAG
301 tgctacgacc cgtctgtcta ggggt
```

EXON 2 (M14296)

$$\overset{C}{\downarrow}$$

```
1   cccgtccgtt gagccttctg tgcctgcagA TGCTAGGTAA CAAGCGACTG GGGCTGTCCG
61  GACTGACCCT CGCCCTGTCC CTGCTCGTGT GCCTGGGTGC GCTGGCCGAG GCGTACCCCT
121 CCAAGCCGGA CAACCCGGGC GAGGACGCAC CAGCGGAGGA CATGGCCAGA TACTACTCAG
181 CGCTGGGACA CTACATCAAC CTCATCACCA GGCAGAGgtg ggtgggaccg cgggaccgat
241 tccggga
```

EXON 3 (M14297)

```
1   acttgctttta aaagactttt tttttttccag ATATGGAAAA CGATCTAGCC CAGAGACACT
61  GATTTCAGAC CTCTTGATGA GAGAAAGCAC AGAAAATGTT CCCAGAACTC Ggtatgacaa
121 ggcttgtgat ggggacattg tt
```

EXON 4 (M14298)

```
1   CCTTACATGC TTTGCTTCTT ATGTTTTACA Ggcttgaaga ccctgcaatg tggtgatggg
61  aaatgagact tgctctctgg cctttttccta ttttcagccc atatttcatc gtgtaaaacg
121 agaatccacc catcctacca atgcatgcag ccactgtgct gaattctgca atgttttcct
181 ttgtcatcat tgtatatatg tgtgtttaaa taaagtatca tgcattcaaa agtgtatcct
241 cctcaatgaa aaatctatta caatagtgag gattattttc gttaaactta ttattaacaa
```

FIG. 1B

HUMAN NEUROPEPTIDE Y (NPY) mRNA

K01911

```
                                                      c
                                                      ↓
1    accccatccg ctggctctca cccctcggag acgctcgccc gacagcatag tacttgccgc
61   ccagccacgc ccgcgcgcca gccaccatgc taggtaacaa gcgacOgggg ctgtccggac
121  tgaccctcgc cctgtccctg ctcgtgtgcc tgggtgcgct ggccgaggcg tacccctcca
181  agccggacaa cccgggcgag gacgcaccag cggaggacat ggccagatac tactcggcgc
241  tgcgacacta catcaacctc atcaccaggc agagatatgg aaaacgatcc agcccagaga
301  cactgatttc agacctcttg atgagagaaa gcacagaaaa tgttcccaga actcggcttg
361  aagaccctgc aatgtggtga tgggaaatga gacttgctct ctggcctttt cctatttca
421  gcccatattt catcgtgtaa aacgagaatc cacccatcct accaatgcat gcagccactg
481  tgctgaattc tgcaatgttt tcctttgtca tcattgtata tatgtgtgtt taaataaagt
541  atcatgcatt c
```

FIG. 1C

DIAGNOSIS OF A PERSON'S RISK OF DEVELOPING ATHEROSCLEROSIS OR DIABETIC RETINOPATHY BASED ON LEUCINE 7 TO PROLINE 7 POLYMORPHISM IN THE PREPRO-NEUROPEPTIDE Y GENE

FIELD OF THE INVENTION

This invention relates to methods for diagnosing a person's susceptibility for having an increased risk for the development of atherosclerosis and a diabetic person's susceptibility for having an increased risk for the development of diabetic retinopathy. The invention relates further to methods for treating persons diagnosed for having increased risk for the development of said diseases, in order to prevent the development of said diseases. The invention also concerns method to investigate or screen pharmaceuticals or genetic aims useful in the treatment of said diseases, by using an animal model including a transgenic animal.

BACKGROUND OF THE INVENTION

The publications and other materials used herein to illuminate the background of the invention, and in particular, cases to provide additional details respecting the practice, are incorporated by reference.

Neuropeptide Y (NPY) is a member of the pancreatic polypeptide family and neuromodulator that is secreted widely by neurons of the central and peripheral nervous systems and it is the most abundant peptide in the brain and in the heart (1–4). NPY is the most potent orexigenic neuropeptide and may have tonic inhibitory action on leptin mediated satiety signal (2–3, 5). NPY stimulates insulin secretion (6) and insulin-induced glucose uptake in normal rate (7). In contrast, insulin and insulin-like growth factor II suppress hypothalamic NPY release (8). In animal models of obesity and Type 2 diabetes, enhanced activity of NPY neurons due to hypothalamic resistance of insulin inhibition may contribute to hyperphagia, reduced energy expenditure and obesity (9). Further, NPY participates in the control on hypothalamic-pituitary-adrenal axis (10). In the cardiovascular system NPY is a vasoconstrictor, it inhibits the release of norepinephrine and potentiates the norepinephrine response (11). Interestingly, in experimental diabetes cardiorespiratory responses to NPY have been shown to be altered (12–13). Further, NPY may have angiogenic properties (4) that could enhance the development of atherosclerosis. The widespread effects of NPY are mediated by several different subtypes of NPY receptors (14). We identified a rather common leucine7 to proline7 polymorphism (Leu7/Pro) very recently (15). This polymorphism was found to be associated with significantly higher serum total- and LDL cholesterol levels particularly in obese subjects in two independent Finnish and one Dutch study population. Further, apolipoprotein B levels were elevated in non-diabetic subjects with Leu7/Pro-polymorphism in one of these populations (15). Although the biochemical and physiological link between cholesterol metabolism and NPY is currently not known, the Leu7/Pro-polymorphism of NPY gene should be considered as a new genetic marker for high cholesterol levels in obese subjects.

SUMMARY OF THE INVENTION

According to one aspect, this invention concerns a method for diagnosing a person's susceptibility for having an increased risk for the development of atherosclerosis, said method comprising determining whether said subject has a polymorphism in the signal peptide part of the human preproNPY, said polymorphism comprising the substitution of the position 7 leucine for proline in the signal peptide part of said preproNPY, said polymorphism being indicative of an increased risk for the development of atherosclerosis.

According to another aspect, the invention concerns a method for diagnosing a diabetic person's susceptibility for having an increased risk for the development of diabetic retinopathy, said method comprising determining whether said subject has a polymorphism in the signal peptide part of the human preproNPY, said polymorphism comprising the substitution of the position 7 leucine for proline in the signal peptide part of said preproNPY, said polymorphism being indicative fo an increased risk for the development of diabetic retinopathy.

According to a third aspect, the invention concerns a method for treating a person, diagnosed for having an increased risk for the development of diabetic retinopathy, for the prevention of developing any of said diseases, comprising administering to said person an effective amount of an agent counteracting the influence of the mutated NPY gene.

According to a fourth aspect, the invention concerns a method for treating a person, diagnosed for having an increased risk for the development of atherosclerosis, or for treating a diabetic person, diagnosed for having an increased risk for the development of diabetic retinopathy, for the prevention of developing any of said diseases, comprising subjecting the person to specific gene therapy aimed to repair the mutated NPY signal peptide sequence.

According to a fifth aspect, the invention concerns a method to investigate or screen pharmaceuticals or genetic aims useful in the treatment of atherosclerosis or diabetics retinopathy, by using an animal model including a transgenic animal which carries a human DNA sequence comprising a nucleotide sequence encoding a prepro-neuropeptide Y (preproNPY) or part thereof encoding mature human NPY peptide, where the leucine amino acid in position 7 of the signal peptide part of said preproNPY i) is unchanged or ii) has been replaced by proline.

According to a sixth aspect, the invention concerns a method to investigate or screen pharmaceuticals or genetic aims useful in the treatment of atherosclerosis or diabetic retinopathy, by using an animal model including a transgenic animal, which carries a DNA sequence comprising a nucleotide sequence encoding otherwise normal mouse NPY sequence or part thereof encoding mature mouse NPY peptide, but in which the nucleotide sequence encoding the mouse signal peptide is replaced by human signal peptide sequence encoding either normal or mutated human signal peptide.

BRIEF DESCRIPTION OF THE DRAWINGS

FIG. 1b shows the nucleotide sequence of the human NPY gene. Upper case indicates exonic sequences and lower case intronic sequences. Genbank accession numbers are given in parenthesis. The arrow shows the position in which thymidine (T) of the normal gene is replaced by cytosine (C) to give the mutant gene. The underlined sequence in Exon 2 is the sequence encoding the signal peptide fo 28 amino acids (Exon 1 is SEQ ID NO:1, exon 2 is SEQ ID NO: 2, exon 3 is SEQ ID NO: 3 and exon 4 is SEQ ID NO:4), and FIG. 1c shows the nucleotide sequence of the human preproNPY mRNA (SEQ ID NO:5, with the protein sequence set forth in SEQ ID NO: 6). The arrow shows the position in which thymidine (t) of the normal mRNA is replaced by cytosine (c) to give the mutant mRNA.

DETAILED DESCRIPTION OF THE INVENTION

Figure 1A:
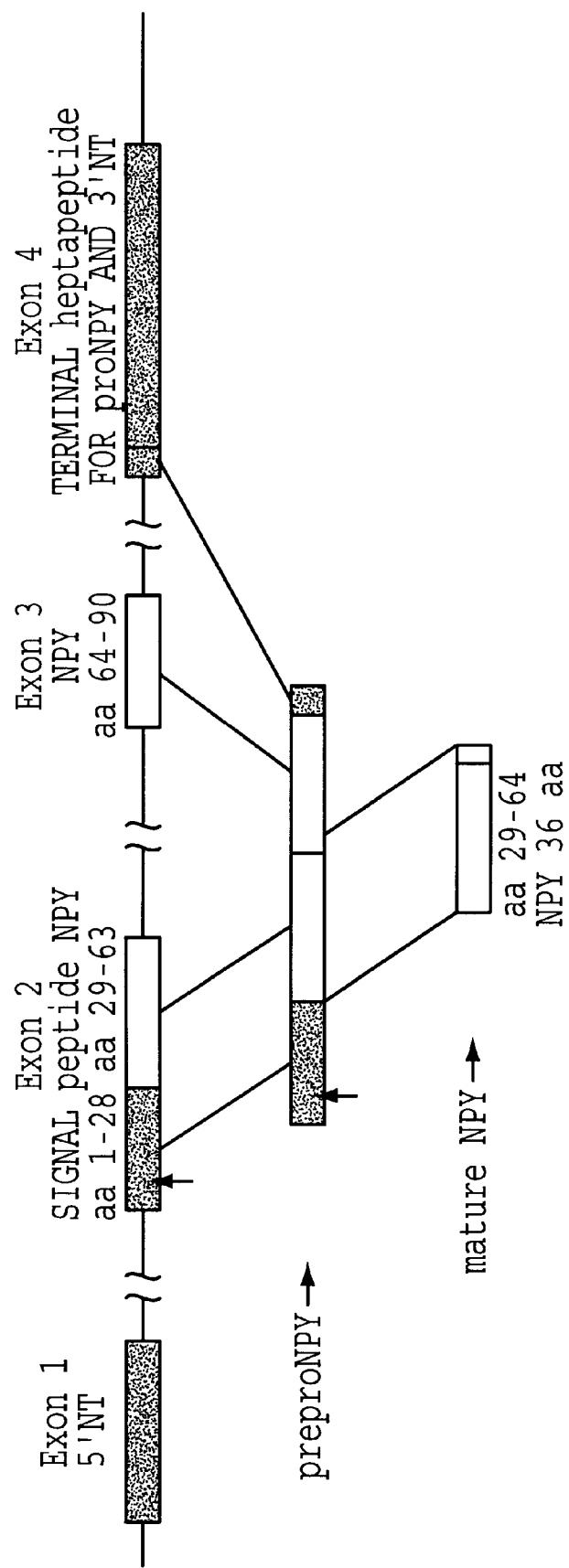
FIG. 1a illustrates schematically the molecular structure of the human NPY gene, the preproNPY peptide and the mature NPY peptide.

Neuropeptide Y (NPY) is a 36-amino-acid neurotransmitter widely present in the central and peripheral nervous systems. NPY has multiple actions, which control body energy balance and cardiovascular function. We have recently demonstrated that the subjects having Pro7 in the signal peptide of NPY have higher serum cholesterol and apolipoprotein B levels when compared to individuals having wildtype (Leu7/Leu7) signal peptide sequence. The present invention is based on a study of the association of Leu7 to Pro polymorphism of the NPY gene with common carotid intima-media-thickness (IMT) assessed by ultrasonography cross-sectionally from the 10-year follow-up study of newly diagnosed patients with Type 2 diabetes (81 patients, 41 males, mean age 67.1 years) and in non-diabetic subjects (105 subjects, 48 males, mean age 65.5 years) who were genotyped for Leu7Pro polymorphism in preproNPY gene. The carrier frequency of the Pro7 substitution was 9.9% in diabetic patients and 14.3% in control subjects ($p=0.360$). The mean common carotid IMT was in non-diabetic subjects without Leu7Pro polymorphism $1.04\pm0.02$ and with it $1.14\pm0.04$ mm ($p=0.156$) and in diabetic patients $1.18\pm0.03$ and covariance of the entire group the mean common carotid IMT was independently associated with the Leu7Pro-polymorphism ($F=5.165$, $p=0.024$). The model included age, gender, diabetes, clinical macrovascular disease, smoking, systolic blood pressure and LDL-cholesterol. Furthermore, diabetic patients having the Pro7 in preproNPY had significantly more often diabetic retinopathy ($p=0.04$) when compared to patients with the Leu7/Leu7 genotype. The present study indicates that the presence of Pro7 substitution in the preproNPY is strongly associated with increased carotid atherosclerosis in diabetic and non-diabetic subjects, even after adjustment for known risk factors. Furthermore, this is the first evidence that Pro7 in the preproNPY increases the risk of type 2 diabetic patients to develop diabetic retinopathy.

The DNA sequence or the mutant signal peptide or said peptide associated with any other cleavage product of pre-proNPY can be used for screening a subject to determine if said subject is a carrier of a mutant NPY gene.

The determination can be carried out either as a DNA analyse according to well known methods, which include direct DNA sequencing of the normal and mutated NPY gene, allele specific amplification using the polymerase chain reaction (PCR) enabling detection of either normal or mutated NPY sequence, or by indirect detection of the normal or mutated NPY gene by various molecular biology methods including e.g. PCR- single stranded conformation polymorphism (SSCP)-method or denaturing gradient gel electrophoresis (DGGE). Determination of the normal or mutated NPY gene can also be done by sing restriction fragment length polymorphism (RFLP)-method, which is particularly suitable for genotyping large number of samples.

The determination can also be carried out at the level of RNA by analysing RNA expressed at tissue level using various methods. Allele spesific probes can be designed for hybridization. Hybridization can be done e.g. using Northern blot, RNase protection assay or in situ hybridization methods. RNA derived form the normal or mutated NPY gene can also be analysed by converting tissue RNA first to cDNA and thereafter amplifying cDNA by an allele spefic PCR-method and carrying out the analysis as for genomic DNA as mentioned above.

Alternatively, the determination can be carried out as an immunoassay where a sample is contacted with an antibody capable of binding the signal peptide or said peptide associated with any other cleavage product of preproNPY. Antibodies can be raised against normal or mutated preproNPY or more specifically against normal or mutated signal peptide part of the NPY. The production of antibodies can be done in experimental animals in vivo to obtain polyclonal antibodies or in vitro using cell lines to obtain monoclonal antibodies.

A person diagnosed for having an increased risk for the development of atherosclerosis, or a diabetic person, diagnosed for having an increased risk for the development of diabetic retinopathy, can be treated for the prevention of developing any of said diseases administering to said subject an effective amount of an agent counteracting the influence of the mutated NPY gene. This can be done by specific gene therapy aimed to repair the mutated NPY sequence, or by administering pharmacotherapies, which are aimed to modulate synthesis, release or metabolism of the endogenous NPY, or to interact in a specific manner at NPY target sites by modulating effects of NPY with specific NPY receptor proteins. Currently, five difference subtypes of NPY receptors have been cloned and characterized (Y1–Y5 receptors) and drug molecules specifically interacting with these NPY receptors have been synthesized. The pharmacotherapy described is not limited to only these named receptors or mechanisms, but also covers other NPY receptors and related mechanisms to be discovered including the secretion of NPY.

Influence of the mutated NPY sequence on the function of NPY gene can be investigated in transgenic animals. A transgenic animal can be generated using targeted homologous recombination methodology. Both normal and mutated sequence of human NPY signal peptide (or any DNA sequence comprising a nucleotide sequence encoding a prepro-neuropeptide Y (preproNPY) or part thereof encoding the amino acid sequence of the mature mouse or human mature NPY peptide, where either i) the leucine amino acid in position 7 of the signal peptide part of said preproNPY has been replaced by proline or II) the leucine amino acid in position 7 of the signal peptide part of said preproNPY is unchanged) will be introduced into the sequence of NPY gene to replace the endogenous signal peptide sequence. Under these conditions, the endogenous NPY gene functions otherwise normally, but the synthesis of the preproNPY is regulated by either normal or mutated human NPY signal peptide sequence. This transgenic model can be used to investigate in a very specific manner the physiological importance of the mutated NPY gene. It also will provide an ideal preclinical model to investigate and screen new drug molecules, which are designed to modify the influence of the mutated NPY gene.

The invention is described more in detail in the following experiments.

EXPERIMENTAL

Study design

This study was a cross-sectional analysis from the 10-year examination of a cohort of patients with Type 2 diabetes and nondiabetic control subjects followed up from the time of diagnosis, as described earlier in detail (16–22). In brief, the original study comprised 133 patients with newly diagnosed Type 2 diabetes, aged 45 to 64 years, and 144 nondiabetic control subjects randomly selected from the population register. The baseline study was carried out during the years 1979–81 and all subjects were collected from a defined area in Eastern Finland (16). All the subjects were invited for the 5- and 10-year follow-up examinations during the years 1985–86 (17) and 1991–92 (18–19), respectively. During the 10-year follow-up 36 (27%) diabetic patients and eight (6%) nondiabetic subjects died, mainly due to cardiovascular diseases (18). At the 10-year examination, carotid ultrasonographic examinations (20–21) were performed for 84 (63%) of the original diabetic and 119 (83%) of the nondiabetic populations and genotype analysis was made for all these except for three diabetic and one non-diabetic subject. The study was approved by the Ethics Committee of the University of Kuopio.

Subjects and methods

The assessment of medical history and cardiovascular diseases, the use of medication, smoking, blood pressure, body-mass index (HMI) and waist-to-hip circumference ratio have been describe din detail previously (18–22). The group "macrovascular disease" refers to subjects with any previously defined evidence of myocardial infarction, stroke or intermittent claudication. An oral glucose tolerance test was performed by using a glucose dose of 75 g. The impaired glucose tolerance in control subjects was classified according to the WHO criteria (23). The collection of blood specimens and the measurement of serum lipid and lipoproteins by ultracentrifugation and precipitation methods apolipoprotein B, plasma glucose and plasma insulin have been likewise presented previously (19–22).

Genotype analysis

PreproNPY genotype was determined by restriction fragment length polymorphism (RFLP) analysis from DNA extracted from the subjects peripheral blood by an investigator unaware of phenotype. Briefly, the polymorphism appears as a thymidine(1128) to cytosine(1128) substitution generating a Bsi EI restriction site, which was used to genotype the subjects for the Leu7Pro polymorphism, as described previously (15). The PCR products were digested by Bsi EI (New England Biolabs, Inc. Beverly Mass. USA) and digestions were analyzed by electrophoresis on 2% agarose gel.

Assessment of carotid atherosclerosis

The high-resolution B-mode ultrasongraphic imaging protocol was designed to ensure the valid and reliable identification of arterial carotid references and the definition of near-wall and far-wall interfaces, as described previously in more detail (20–21,24). Briefly, the carotid artery was divided into two segments on the basis of arterial anatomy and geometry. The key anatomic features defining these segments were the proximal origin of the bulb (carotid bifurcation) and the tip of the flow divider, which separates internal from external carotid arteries. In longitudinal arterial images, the adventitia-media and the intima -lumen interfaces on the far wall were the specific anatomic boundaries defining the IMT. Two certified sonographers performed the carotid ultrasound examinations. A Biosound Phase Two ultrasound device equipped with a 10-MHz annular array probe was used. Video-recorded examinations were quantitatively analyzed at a central laboratory using a computer-assisted reading procedure (24–25). The mean maximum of the far wall bilaterally was used as the measurement of the common carotid IMT.

Statistical methods

Our a priori hypotheses was that the subjects having Pro7 substitution in preproNPY have higher mean IMT compared to the subjects having wild type preproNPY (Leu7/Leu7). Associations of Leu7Pro polymorphism with continuous variables were calculated using Student's t-test and for categorized variables by Chi square test. The association of common carotid IMT with Leu7Pro polymorphism was further analyzed by analysis of covariance (ANCOVA) controlling for the effects of selected covaniates. Variables with skewed distribution (eg. carotid IMT, insulin) were analyzed after logarithmic transformation. P-value equal or less than 0.05 was considered statistically significant. All statistical analyses were conducted with procedures from SPSS-Unix.

Results

The frequency of C1128 allele frequencies was not significantly different between non-diabetic (14.3%) and diabetic (9.9%, p=0.36) groups. The characteristics of non-diabetic and diabetic subjects for Leu7/Leu7 and Pro7/-groups are presented in Tables $1a \geq b$. No differences in age, gender, body mass index, waist-to-hip-ratios, blood pressure levels and the frequencies of macrovascular disease were found between the genotype groups within the non-diabetic and diabetic groups. LDL-cholesterol was higher in non-diabetic subjects with Leu7/Pro-polymorphism than in those without p=0.05), as we have reported previously (15). although apolipoprotein B levels tended to be higher in Pro7/-group than in Leu7/Leu7-group, the differences wee not statistically significant. Our previous study included only lean subjects without any medication known to affect cholesterol metabolism (like beta-blockers or diuretics) of the present non-diabetic group (15). In other lipoproteins no evident differences were found, and interestingly, in diabetic patients there was no association with serum cholesterol, even when subjects were analyzed according to median body mass index (data not shown).

The mean common carotid IMT was about 25% higher in diabetic patients with Pro7 allele than in those without it (p=0.440) and the respective increase in IMT was 9% in non-diabetic subjects (p=0.156). In the analysis of covariance both groups combined (Table 2) the independent predictors of common carotid IMT were age, Pro7 allele, diabetes, systolic blood pressure, and macrovascular disease. Furthermore, those diabetic patients having the Pro7 substitution in the preproNPY had significantly accelerated rate of diabetic retinopathy (p=0.04), when compared to diabetics with the Leu7/Leu7-genotype.

Discussion

Our findings based on elderly Finnish non-diabetic and diabetic subjects indicates that the Pro7 allele of preproNPY is strongly associated with increased carotid atherosclerosis, and even more markedly in diabetic patients. This finding is of importance, because an increase in the thickness of IMT of carotid arteries increases the risk for cardiovascular events in a linear fashion even before clinical manifestations of cardiovascular disease (26). In addition, the presence of Pro7 polymorphism in the preproNPY was significantly associated with the rate of diabetic retinopathy. The Pro 7 allele was also associated with high serum LDL cholesterol levels and apolipoprotein B-levels in lean non-diabetic subjects (15), but this was not found in diabetic patients regardless of their body weight.

Type 2 diabetes is a state characterized by markedly increased risk of atherosclerosis and although known risk factors contribute largely to the occurrence of diabetic macrovascular diseases (27), a large proportion of this vascular burden remains unexplained and search for other potential environmental, metabolic and genetic contributors are warranted. In this study we show for the first time that diabetic patients with Pro7 allele have higher carotid IMT than those with Leu7/Leu7-genotype. Although this finding was based on a limited number of subjects, the lack of association of Pro7 allele with other risk factors measured in diabetic patients makes the finding more intriguing. As non-diabetic control group included subjects with impaired glucose tolerance as any population-based study does and therefore, glucose tolerance is in a way continuum in this study population, we combined the groups in order to increase the statistical power of the study for the analysis of covariance. In this analysis age, diabetes, systolic blood pressure and clinical macrovascular disease were, as previously reported (21), powerful explanatory variables of carotid IMT. Interestingly, the effect of NPY genotype remained statistically significant in this analysis. Other cardiovascular risk factors except fasting insulin in non-diabetic subjects were not associated with NPY genotype in either group. The selective mortality may cause bias in the interpretation, as in any cross-sectional analysis. However, as LDL-cholesterol-levels were constantly higher during the whole 10-year follow-up in lean non-diabetic control subjects with PRO7 allele and, on the other hand, the genotype effect on carotid IMT was more marked in diabetic patients who had high cardiovascular mortality form the time of diagnosis (18), it is likely that this study under-estimates this association.

Why could then NPY enhance the development of atherosclerosis? First, this effect may be mediated by the effects of the PreproNPY genotype on LDL-cholesterol metabolism (15). However, this effect is modulated by body weight (15) and as judged from the present study, no effect was seen in Type 2 diabetic patients in this regard (more detailed analysis of lipoproteins assessed either cross-sectionally or longitudinally gave no further insights in this regard). Second, NPY may have angiogenic properties that could be implicated in the development of atherosclerosis. NPY has been shown to act as a smooth muscle mitogen (28), to stimulate attachment, migration, DNA synthesis (29), and the formation of capillary tubes by human endothelial cells (4). Minor proportion of circulating NPY level is derived form endothelial cells and this endothelially derived NPY may act as an autocrine angiogenic factor even at very low concentrations (4). Subjects with Pro7 substitution in preproNPY may therefore be predisposed to increased arterial wall thickening seen as increased intima-media thickening of carotid arteries, because of impaired function of endothelial NPY. Third, NPY is an important modulator of autonomic nervous system. Majority of circulating NPY is derived from the perivascular sympathetic nerve endings, and the level of NPY is correlated to those of norepinephrine (30). Autonomic nervous dysfunction is an independent predictor of cardiovascular mortality in patients with Type 2 diabetes, as demonstrated form this study population (22). The mechanisms behind cardiovascular disease and autonomic nervous dysfunction are speculative, but our unpublished observations suggest that cardiac autonomic regulation is altered in subjects with those with Pro7 substitution in the preproNPY. Therefore, we suggest that atherosclerosis may be associated with gene(s) involved in vascular development, lipid metabolism and autonomic nervous function and the recently found gene variant (15) in NPY is the first one in this respect shown to be related to accelerated atherosclerosis.

In conclusion, these results indicate that the presence of Pro7 substitution in the preproNPY is associated with ultrasonographically assessed carotid atherosclerosis in Finnish diabetic and non-diabetic subjects. Furthermore, this study provides first evidence that the Pro7 in the preproNPY is also associated with increased rate of diabetic retinopathy in NIDDM (Type 2 diabetes) patients, which could be potential target for drug development.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

TABLE 1A

The clinical characteristics of the study population according to Leu7/Pro-genotype in nondiabetic subjects

| Characteristic | Leu7/Leu7 n = 90 | Pro7/- n = 15 | p-value |
|---|---|---|---|
| Age (years) | 65.5 ± 0.6 | 65.5 ± 1.1 | 0.982 |
| Male gender (n, %) | 43 (48) | 5 (33) | 0.295 |
| Body-mass Index (kg/m$^2$) | 27.8 ± 0.5 | 28.4 ± 1.2 | 0.611 |
| Macrovascular disease (n, %) | 11 (12) | 4 (27) | 0.139 |
| Smoking history (n, %)) | 23 (26) | 5 (33) | 0.528 |
| Treatment for hypertension (n, percentage) | 26 (29) | 6 (40) | 0.387 |
| Systolic blood pressure (mmHg) | 149 ± 2 | 148 ± 3 | 0.863 |
| Diastolic blood pressure (mmHg) | 85 ± 1.1 | 85 ± 3 | 0.847 |
| Fasting serum insulin (mU/L) | 11.0 ± 0.6 | 14.8 ± 2.2 | 0.056 |
| Impaired glucose tolerance (n, %) | 11 (12) | 1 (7) | 0.531 |
| Mean of common carotid IMT (mm) | 1.04 ± 0.02 | 1.14 ± 0.4 | 0.156 |
| Serum apolipoprotein B (mg/L) | 1.04 ± 0.03 | 1.12 ± 0.08 | 0.285 |
| Serum HDL cholesterol (mmol/L) | 1.34 ± 0.03 | 1.27 ± 0.30 | 0.403 |
| Serum LDL cholesterol (mmol/L) | 4.11 ± 0.09 | 4.61 ± 0.30 | 0.05 |
| Serum total cholesterol (mmol/L) | 6.29 ± 0.11 | 6.72 ± 0.37 | 0.153 |
| Serum triglycerides (mmol/L) | 1.81 ± 0.12 | 1.65 ± 0.18 | 0.811 |
| Waist-to-hip ratio | 0.91 ± 0.01 | 0.91 ± 0.03 | 0.926 |

TABLE 1B

The clinical characteristics of the study population according to Leu7/-Pro-genotype in diabetic subjects

| Characteristic | Leu7/Leu7 n = 73 | Pro7/- n = 8 | p-value |
|---|---|---|---|
| Age (years) | 67.1 ± 0.7 | 66.5 ± 1.2 | 0.765 |
| Male gender (n, %) | 36 (49) | 5 (63) | 0.479 |
| Body-mass Index (kg/m$^2$) | 29.4 ± 0.6 | 27.6 ± 4.1 | 0.344 |
| Macrovascular disease (n, %) | 28 (38) | 5 (63) | 0.187 |
| Smoking history (n, %)) | 25 (34) | 2 (25) | 0.598 |
| Treatment for hypertension (n, percentage) | 40 (55) | 5 (63) | 0.677 |
| Systolic blood pressure (mmHg) | 154 ± 2.8 | 150 ± 10.3 | 0.637 |
| Diastolic blood pressure (mmHg) | 84 ± 2 | 87 ± 4 | 0.482 |
| Fasting serum insulin (mU/L) | 15.0 ± 0.9 | 15.7 ± 3.7 | 0.823 |
| Mean of common carotid IMT (mm) | 1.18 ± 0.03 | 1.58 ± 0.21 | 0.004 |
| Serum apolipoprotein B (mg/L) | 1.17 ± 0.03 | 1.00 ± 0.09 | 0.10 |
| Serum HDL cholesterol (mmol/L) | 1.11 ± 0.03 | 1.27 ± 0.12 | 0.142 |
| Serum LDL cholesterol (mmol/L) | 4.09 ± 0.10 | 3.66 ± 0.27 | 0.204 |
| Serum total cholesterol (mmol/L) | 6.44 ± 0.16 | 5.95 ± 0.36 | 0.325 |
| Serum triglycerides (mmol/L) | 2.62 ± 0.22 | 2.09 ± 0.34 | 0.455 |
| Waist-to-hip ratio | 0.94 ± 0.01 | 0.98 ± 0.03 | 0.222 |

TABLE 2

Analysis of covariance for mean carotid intima-media-thickness adjusting for the effects of Leu7/Propolymorphism and covariates in the combined cohort

| Risk Factor | F-value | Significance |
| --- | --- | --- |
| Age | 7.744 | 0.006 |
| Gender | 2.866 | 0.092 |
| Diabetes | 3.960 | 0.046 |
| NPY Leuy/Pro | 5.165 | 0.024 |
| Macrovascular disease | 4.278 | 0.040 |
| Smoking history | 2.225 | 0.138 |
| Systolic blood pressure | 5.754 | 0.018 |
| LDL-cholesterol | 0.142 | 0.707 |

2-way interaction: diabetes X NPY Leu7/Pro F = 0.174, p = 0.677

REFERENCES

1. Benarroch EE: Neuropeptides in the sympathetic system: presence, plasticity, modulation, and implications. *Ann Neurol* 36: 6–13, 1994

2. Tomaszuk A, Simpson C, Williams G: Neuropeptide Y, the hypothalamus and the regulation of energy homeostasis, *Horm Res* 46: 53–8, 1996

3. Palmiter RD. Erickson JC, Hollopeter G, Baraban SC, Schwatrz MW: Life without neuropeptide Y. *Recent Prog Horm Res* 53: 163–99, 1998

4. Zukowska-Grojec Z. Karwatowska-Prokopczuk, E, Rose W, Rone J. Movafagh S, Ji H. Yeh Y. Chen WT, Kleinam Hk, Grouzmann E, Grant DS: Neuropeptide Y: a novel angiogenic factor from the sympathetic nerves and endothelium. *Circ Res* 83: 187–95, 1998

5. Sahu A, Kalra SP: Neuropeptide regulation of feeding behaviour Neuropeptide Y: *TEM* 4: 217–224, 1993

6. Moltz JH, McDonald JK: Neuropeptide Y: direct and indirect action on insulin secretion in the rat. *Peptides* 6:115–1159, 1985

7. Vettor R, Pagano C. Granzotto M, Englaro P, Angeli P, Blum WF, Federspil G, Rohner-Jeanrenaud F, Jenarenaud B: Effects of intravenous neuropeptide Y on insulin secretion and insulin sensitivity on skeletal muscle in normal rats. *Diabetologia* 41: 1361–7, 1998

8. Sahu A, Dube MG, Phelps CP, Sninsky CA, Kalra PS, Kalra SP: Insulin and insulin-like growth factor II suppress neuropeptide Y release from the nerve terminals in the paraventricular nucleus: a putative hypothalamic site for energy homeostasis. *Endocrinology* 136: 5718–24, 1995

9. Franksih HM, Dryden S, Hopkins D, Wang Q, Williams G: Neuropeptide Y, the hypothalamus, and diabetes: insights into the central control of metabolism. *Peptides* 16: 757–71, 1995

10. Wahlestedt C, Skagerberg G, Ekman R, Heilig M, Sundler F, Hakanson R: Neuropeptide Y (NPY) in the area of the hypothalamic paraventricular nucleus activates the pituitary-adrenocortical axis in the rat. *Brain Res* 417:33–38, 1987

11. Shine J, Potter EK, Biden T, Selbie LA, Herzog H: Neuropeptide Y and regulation of the cardiovascular system. *J Hypertens* (Suppl) 12:S41–S45, 1994

12. Dunbar JC, Ergene E, Anderson GF, Barraco RA: Decreased cardiorespiratory effects of neuropeptide Y in the nucleus tractus solitarius in diabetes. *Am J Physiol* 262: R865–71, 1992

13. Lind H, Brlinge D, Brunkwall J. Edvinsson L: Selective attenuation of neuropeptide-Y-mediated contractile responses in blood vessels from patients with diabetes mellitus. *Clin Auton Res* 5: 191–7, 1995

14. Larhammar D, Söderberg C, Lundell I: Evolution of the neuropeptide Y famil and its receptors. *Ann NY Acad Sci* 839: 35–40, 1998

15. Karvonen MK, Pesonen U, Koulu M, Niskanen L, Laakso M, Rissanen A, Dekker JM, Hart LM, Valve R, Uusitupa MIJ: Association of a leucine (7)0-to -proline (7) polymorphism in the signal peptide of neuropeptide Y with high serum cholesterol and LDL cholesterol levels. *Nat Med* 4: 1434–1437, 1998

16. Uusitupa M, Siitonen O, Aro A, Pyörälä K: Prevalence of coronary heart disease, left ventricular failure and hypertension in middle-aged, newly diagnosed type 2 (non-insulin-dependent) diabetic subjects. *diabetologia* 28: 22–27, 1985

17. Niskanen LK, Uusitupa MI, Sarlund H, Siitonen O, Pyörälä K: Five-year follow-up study on plasma insulin levels in newly diagnosed NIDDM patients and nondiabetic subjects. *Diabetes Care* 13: 41–28, 1990

18. Dusitupa MIJ, Niskanen LK, Siitonen O, Voutilainen E. Pyörälä K: Ten-year cardiovascular mortality in relation to risk factors and abnormalities in lipoprotein composition in type 2 (non-insulin-dependent) diabetic and non-diabetic subjects. *Diabetologia* 36: 1175–1184, 1993

19. Niskanen L, Uusitupa M, Krjalainen J. Siitonen O: Metabolic evolution of Type 2 diabetes -10-year follow-up study. *J Intern Med* 236: 263–270, 1994

20. Uusitupa M. Niskanen L, Luoma J, Mercouri M, Rauramaa R, Ylä-Herttuala S: Autoantibodies against oxidized LDL as predictors of atherosclerotic vascular disease in non-insulin-dependent diabetes mellitus. *Arterioscl & Thromb & Vasc Biol* 1236–1242, 1996

21. Niskanen L, Rauramaa R, Miettinen H, Haffner SM, Mercuri M, Uusitupa M: Carotid artery intima-media thickness in elderly patients with NIDDM and in nondiabetic subjects. *Stroke* 27: 1986–1992, 1996

22. Töyry J, Miskanen L, Mäntysaari M. Länsimies e, Uusitupa M: Occurrence, predictors, and clinical significance of autonomic neuropathy in NIDDM: 10-year follow-up from the diagnosis. *Diabetes* 45: 308–315, 1996

23. World Healths Organization. Diabetes mellitus: report of a WHO Study Group. Geneva: World Health Org., Tech Rep Ser, no 727, 1985

24. Mercuri M. Bond M G, Nichols F T, Carr A A, Flack J M, Byington R, Raines J, for the MIDAS Group. Baseline reproducibility of B-mode ultrasound imaging measurements of carotid intimal media thickness: the Multicenter Isradipine Diuretic Atheroslerosis Study (MIDAS). *J Cardiovasc Diagnosis Procedures* 11: 241–252, 1993

25. Rauramaa R, Väisänen S, Mercuri M, Rankinen T, Penttilä I, Bond MG: Association of risk factors and body iron status to carotid atherosclerosis in middle-aged Eastern Finnish men. *Eur Heart J* 15: 1020–1027, 1994

26. O'Leary D H, Polak J F, Kronmal R A, Manolio T A, Burke G L, Wolfon S K J. Carotid-artery intima and media thickness as a risk factor for myocardial infarction and stroke in older adults. Cardiovascular Health Study Collaborative Research Group. *N Engl J Med* 1999: 340: 14–22.

27. Stamler J, Vaccaro O, Neaton J D, Wentworth D for the Multiple Risk Factor Intervention Trial Research Group: Diabetes, other risk factors and 12-years cardiovascular mortality for men screened in the Multiple Risk Factor Intervention Trial. *Diabetes Care* 16: 434–444, 1993

28. Zukowska-Grojec Z, Pruszczyk P, Colton C. Yao J. Shen G H, Myers A K, Wahlestedt C: Mitogenic effect of neuropeptide Y in rat vascular smooth muscle cells. *Peptides* 1993; 14:263–268.

25. Shirgeri Y, Fujimoto M: Neuropeptide Y stimulates DNA synthesis in vascular smooth muscle cells. *Neurosci Lett* 1993; 149:19–22.

30. Lundberg JM, Franco-Cereceda A, Hemsen A, Lacroix J S, Pernow J: Pharmacology of noradrenaline and neuropeptide tyrosine (NPY)-mediated sympathetic cotransmission. *Fundam Clin Pharmacol* 4:373–391, 1990

What is claimed is:

1. A method for diagnosing an individual's susceptibility for having a risk for the development of atherosclerosis, said method comprising analyzing the preproNPY protein in a sample from said individual for a polymorphism comprising the substitution fo proline for leucine at position 7 of said preproNPY, said polymorphism being indicative of a risk of said individual for the development of atherosclerosis.

2. The method according to claim 1 wherein said individual diabetes.

3. A method for diagnosing a diabetic individual's susceptibility for having a risk for the development fo diabetic retinopathy, said method comprising analyzing the preproNPY protein in a sample from said individual for a polymorphism comprising the substitution fo proline for leucine at position 7 of said preproNPY, said polymorphism being indicative fo a risk of said individual for the development fo diabetic retinopathy.

4. A method for diagnosing an individual's susceptibility for having a risk for the development of atherosclerosis, said method comprising analyzing the DNA of the preproNPY gene in a sample from said individual for a mutation in said gene which results in a polymorphism in the preproNPY protein comprising the substitution of proline for leucine at position 7 of said preproNPY protein, said polymorphism being indicative of a risk of said individual for the development of atherosclerosis.

5. A method for diagnosing a diabetic individual's susceptibility of having a risk for the development of diabetic retinopathy, said method comprising analyzing the DNA of the preproNPY gene in a sample from said individual for a mutation in said gene which results in a polymorphism in the preproNPY protein comprising the substitution of proline for leucine at position 7 of said preproNPY protein, said polymorphism being indicative of a risk of said individual for the development of diabetic retinopathy.

6. The method according to claim 4 wherein said individual has diabetes.

* * * * *

SEQUENCE LISTING

```
<160> NUMBER OF SEQ ID NOS: 6

<210> SEQ ID NO: 1
<211> LENGTH: 325
<212> TYPE: DNA
<213> ORGANISM: Homo sapiens

<400> SEQUENCE: 1
ccgcttcttc aggcagtgcc tggggcggga gggttggggt gtgggtggct ccctaagtcg      60
acactcgtgc ggctgcggtt ccagccccct cccccgcca ctcaggggcg ggaagtggcg     120
ggtgggagtc acccaagcgt gactgcccga ggcccctcct gccgcggcga ggaagctcca    180
taaaagccct gtcgcgaccc gctctctgca ccccatccgc tggctctcac ccctcggaga    240
cgctcgcccg acagcatagt acttgccgcc cagccacgcc cgcgcgccag ccaccgtgag    300
tgctacgacc cgtctgtcta ggggt                                          325

<210> SEQ ID NO: 2
<211> LENGTH: 247
<212> TYPE: DNA
<213> ORGANISM: Homo sapiens

<400> SEQUENCE: 2
cccgtccgtt gagccttctg tgcctgcaga tgctaggtaa caagcgactg gggctgtccg      60
gactgaccct cgccctgtcc ctgctcgtgt gcctgggtgc gctggccgag gcgtacccct    120
ccaagccgga caacccgggc gaggacgcac cagcggagga catggccaga tactactcag    180
cgctgggaca ctacatcaac ctcatcacca ggcagaggtg ggtgggaccg cgggaccgat    240
tccggga                                                             247

<210> SEQ ID NO: 3
<211> LENGTH: 142
<212> TYPE: DNA
<213> ORGANISM: Homo sapiens

<400> SEQUENCE: 3
acttgcttta aaagactttt ttttttccag atatggaaaa cgatctagcc cagagacact      60
gatttcagac ctcttgatga gagaaagcac agaaaatgtt cccagaactc ggtatgacaa    120
ggcttgtgat ggggacattg tt                                             142

<210> SEQ ID NO: 4
<211> LENGTH: 300
<212> TYPE: DNA
<213> ORGANISM: Homo sapiens

<400> SEQUENCE: 4
ccttacatgc tttgcttctt atgttttaca ggcttgaaga ccctgcaatg tggtgatggg      60
```

-continued

```
aaatgagact tgctctctgg cctttcccta ttttcagccc atatttcatc gtgtaaaacg      120
agaatccacc catcctacca atgcatgcag ccactgtgct gaattctgca atgtttttcct    180 ttgtcatcat tgtatatatg tgtgtttaaa taaagtatca tgcattcaaa agtgtatcct    240
cctcaatgaa aaatctatta caatagtgag gattattttc gttaaactta ttattaacaa    300
```

<210> SEQ ID NO: 5
<211> LENGTH: 551
<212> TYPE: DNA
<213> ORGANISM: Homo sapiens
<220> FEATURE:
<221> NAME/KEY: CDS
<222> LOCATION: (87)..(377)
<220> FEATURE:
<221> NAME/KEY: sig_peptide
<222> LOCATION: (87)..(170)

<400> SEQUENCE: 5

```
accccatccg ctggctctca cccctcggag acgctcgccc gacagcatag tacttgccgc     60
ccagccacgc ccgcgcgcca gccacc atg cta ggt aac aag cga ctg ggg ctg     113
                              Met Leu Gly Asn Lys Arg Leu Gly Leu
                                1               5 tcc gga ctg acc ctc gcc ctg tcc ctc gtg tgc ctg ggt gcg ctg          161
Ser Gly Leu Thr Leu Ala Leu Ser Leu Val Cys Leu Gly Ala Leu
 10              15                  20                  25 gcc gag gcg tac ccc tcc aag ccg gac aac ccg ggc gag gac gca cca     209
Ala Glu Ala Tyr Pro Ser Lys Pro Asp Asn Pro Gly Glu Asp Ala Pro
                30                  35                  40 gcg gag gac atg gcc aga tac tac tcg gcg ctg cga cac tac atc aac     257
Ala Glu Asp Met Ala Arg Tyr Tyr Ser Ala Leu Arg His Tyr Ile Asn
            45                  50                  55 ctc atc acc agg cag aga tat gga aaa cga tcc agc cca gag aca ctg     305
Leu Ile Thr Arg Gln Arg Tyr Gly Lys Arg Ser Ser Pro Glu Thr Leu
        60                  65                  70 att tca gac ctc ttg atg aga gaa agc aca gaa aat gtt ccc aga act    353
Ile Ser Asp Leu Leu Met Arg Glu Ser Thr Glu Asn Val Pro Arg Thr
    75                  80                  85 cgg ctt gaa gac cct gca atg tgg tgatgggaaa tgagacttgc tctctggcct   407
Arg Leu Glu Asp Pro Ala Met Trp
90                  95 tttcctattt tcagcccata tttcatcgtg taaaacgaga atccacccat cctaccaatg    467
catgcagcca ctgtgctgaa ttctgcaatg ttttcctttg tcatcattgt atatatgtgt    527
gtttaaataa agtatcatgc attc                                            551
```

<210> SEQ ID NO: 6
<211> LENGTH: 97
<212> TYPE: PRT
<213> ORGANISM: Homo sapiens

<400> SEQUENCE: 6

```
Met Leu Gly Asn Lys Arg Leu Gly Leu Ser Gly Leu Thr Leu Ala Leu
  1               5                  10                  15

Ser Leu Leu Val Cys Leu Gly Ala Leu Ala Glu Ala Tyr Pro Ser Lys
                20                  25                  30

Pro Asp Asn Pro Gly Glu Asp Ala Pro Ala Glu Asp Met Ala Arg Tyr
            35                  40                  45

Tyr Ser Ala Leu Arg His Tyr Ile Asn Leu Ile Thr Arg Gln Arg Tyr
        50                  55                  60

Gly Lys Arg Ser Ser Pro Glu Thr Leu Ile Ser Asp Leu Leu Met Arg
```

-continued

```
                65                  70                  75                  80
Glu Ser Thr Glu Asn Val Pro Arg Thr Arg Leu Glu Asp Pro Ala Met
                        85                  90                  95
Trp
```